(12) United States Patent
Stodola

(10) Patent No.: US 9,351,953 B2
(45) Date of Patent: May 31, 2016

(54) CANNABIS CONVERSION PROCESS

(71) Applicant: Kelly J. Stodola, Coquitlam (CA)

(72) Inventor: Kelly J. Stodola, Coquitlam (CA)

( * ) Notice: Subject to any disclaimer, the term of this patent is extended or adjusted under 35 U.S.C. 154(b) by 0 days.

(21) Appl. No.: 14/457,854

(22) Filed: Aug. 12, 2014

(65) Prior Publication Data

US 2016/0045471 A1  Feb. 18, 2016

(51) Int. Cl.
*A01N 65/00* (2009.01)
*A61K 31/352* (2006.01)
*A61K 36/185* (2006.01)
*A61K 47/46* (2006.01)

(52) U.S. Cl.
CPC .............. *A61K 31/352* (2013.01); *A61K 36/185* (2013.01); *A61K 47/46* (2013.01)

(58) Field of Classification Search
CPC ...................................................... A61K 36/00
USPC ......................................................... 424/725
See application file for complete search history.

(56) References Cited

PUBLICATIONS

Fairbairn et al., "Activity of Cannabis in Relation to Its Delta'-trans-Tetrahydro-Cannabinol Content," Br. J. Pharmac. 1981, 72, p. 401-409.
Menetrey et al., "Assessment of Driving Capability Through the Use of Clinical and Psychomotor Tests in Relation to Blood Cannabinoids Levels Following Oral Administration of 20 mg Dronabinol or of a Cannabis Decoction Made with 20 or 60 mg Delta-9-THC," J. of Analytical Toxicology, vol. 29, Jul./Aug. 2005, p. 327-338.
Romano et al., "Cannabis Oil: chemical evaluation of an upcoming cannabis-based medicine," Cannabinoids, vol. 7, Issue 1, May 5, 2013, p. 1-11.
Iversen, L.L., (2000) "The Science of Marijuana," (2nd Edition) p. 17-18, New York, New York. Oxford University Press, Inc.

*Primary Examiner* — Michael Meller
(74) *Attorney, Agent, or Firm* — Benesch Friedlander Coplan & Aronoff LLP; Kraig K. Anderson

(57) ABSTRACT

A method for preparing an ingestible cannabis composition is provided. Also provided is the ingestible cannabis composition and a kit including the ingestible cannabis composition.

20 Claims, 2 Drawing Sheets

200

200

202
INGESTIBLE CANNABIS COMPOSITION INCLUDING ROASTED CANNABIS AND INGESTIBLE EXCIPIENT

204
INSTRUCTIONS TO INGEST A PORTION OF THE INGESTIBLE CANNABIS COMPOSITION EFFECTIVE TO PROVIDE USER WITH DESIRED DOSAGE

CANNABIS CONVERSION PROCESS

BACKGROUND

There is much recent interest in the use of cannabis for medicinal preparations. Although cannabis has been consumed by humans for thousands of years, deliberate modern medicinal preparations may still benefit from improvements in composition and preparation, particularly for ingestion.

The present disclosure appreciates that preparation of cannabis for ingestion may be a challenging endeavor.

SUMMARY

In various embodiments, a method for preparing an ingestible cannabis composition is provided. The method may include providing a dehydrated cannabis. The method may include heating the dehydrated cannabis under oxygen-limited conditions effective to form a roasted cannabis. The method may include combining the roasted cannabis with an ingestible excipient to form the ingestible cannabis composition.

In various embodiments, an ingestible cannabis composition is provided. The ingestible cannabis composition may include a roasted cannabis. The ingestible cannabis composition may include an ingestible excipient to form the ingestible cannabis composition. The ingestible cannabis composition may be prepared by any method described herein.

In several embodiments, a kit is provided. The kit may include an ingestible cannabis composition. The ingestible cannabis composition may include a roasted cannabis. The ingestible cannabis composition may include an ingestible excipient. The kit may include instructions. The instructions may include directing a user to ingest a portion of the ingestible cannabis composition effective to provide the user with a desired dosage.

BRIEF DESCRIPTION OF THE DRAWINGS

The accompanying figures, which are incorporated in and constitute a part of the specification, illustrate example methods and apparatuses, and are used merely to illustrate example embodiments.

DETAILED DESCRIPTION

Figure 1:
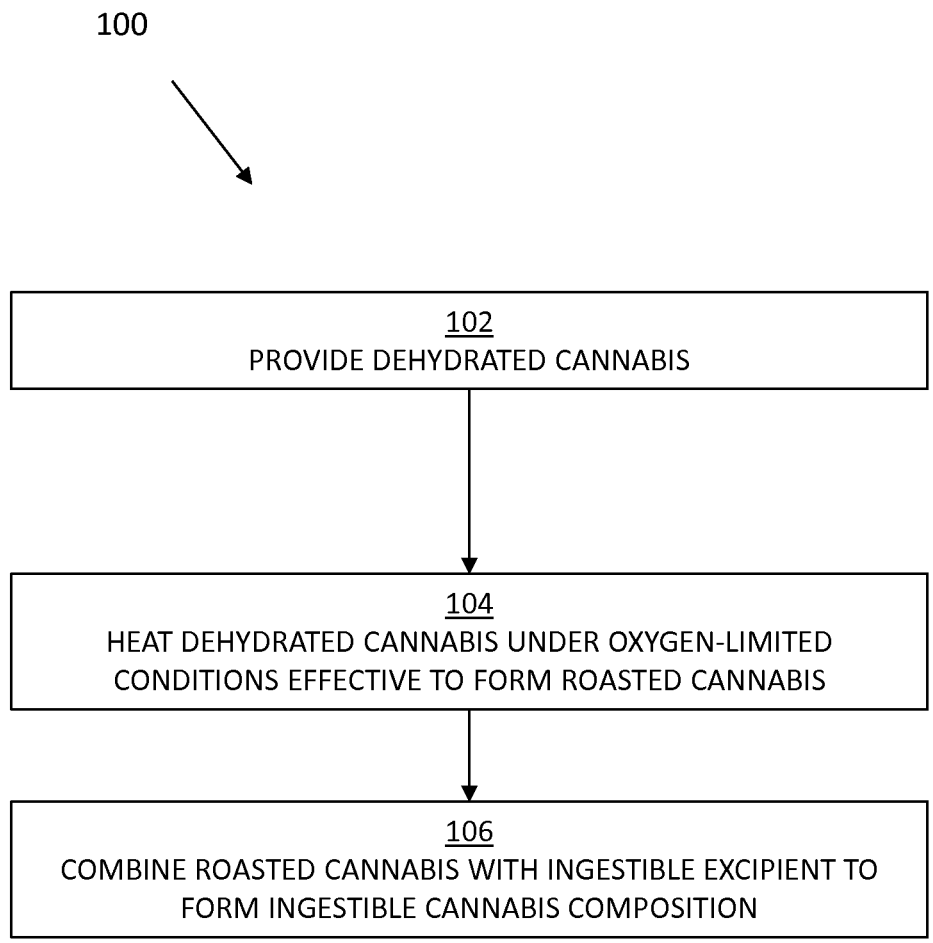
FIG. 1 is a flow diagram describing an example method.

In various embodiments, a method for preparing an ingestible cannabis composition is provided. FIG. 1 is a flow diagram describing an example method 100 for preparing an ingestible cannabis composition. Method 100 may include 102 providing a dehydrated cannabis. Method 100 may include 104 heating the dehydrated cannabis under oxygen-limited conditions effective to form a roasted cannabis. Method 100 may include 108 combining the roasted cannabis with an ingestible excipient to form the ingestible cannabis composition.

In various embodiments, the providing the dehydrated cannabis may include dehydrating cannabis to provide the dehydrated cannabis. The dehydrating may include one or more of: oven drying, sun drying; forced-air drying; drum drying; freeze-drying; vacuum desiccation; chemical desiccation, e.g., in the presence of a hygroscopic chemical desiccant such as silica; supercritical desiccation, e.g., using supercritical water or supercritical carbon dioxide; and the like. The dehydrated cannabis may be characterized by a moisture content in weight percent of less than, or less than about one or more of: 50; 45; 40; 35; 30; 25; 20; 19; 18; 17; 16; 15; 14; 13; 12; 11; 10; 9; 8; 7; 6; 5; 4; 3; 2; 1; or 0.5; or a range between any two of the preceding values, for example, between about 50% and about 0.5%, between about 30% and about 0.5%, between about 20% and about 0.5%, and the like. The providing the dehydrated cannabis may include dehydrating cannabis to provide the dehydrated cannabis. The cannabis to be dehydrated may be any conventional harvested cannabis.

In various embodiments, the heating the dehydrated cannabis under oxygen-limited conditions may include heating to a temperature in °C. of, or of about, one or more of: 115; 120; 125; 130; 130; 131; 132; 133; 134; 135; 136; 137; 138; 138; 140; 141; 142; 143; 144; 145; 146; 147; 148; 149; 150; 155; or 160; or a range of, or a range about, any two of the preceding values in °C. For example, the temperature range in °C. may be between about one or more of: 115 and 155; 120 and 155; 120 and 150; 125 and 155; 125 and 150; 125 and 145; 130 and 155; 130 and 150; 130 and 145; 130 and 140; 135 and 155; 135 and 150; 135 and 145; or 135 and 140. In some embodiments, the temperature in °C. may be, or may be about, one or more of: 130; 131; 132; 133; 134; 135; 136; 137; 138; 138; 140; 141; 142; 143; 144; 145; 146; 147; 148; 149; or 150. In some embodiments, the temperature in °C. may be, or may be about, one or more of: 135; 136; 137; 138; 138; 140; 141; 142; 143; 144; or 145.

In various embodiments, the heating the dehydrated cannabis under oxygen-limited conditions may include heating for a time in minutes of, or of about, one or more of: 15; 20; 25; 30; 35; 40; 45; 50; 55; 60; 90; or 120; or a range between any two of the preceding values, for example, about or between about one or more of: 15 and 55; 15 and 50; 15 and 45; 15 and 40; 15 and 35; 15 and 30; 15 and 25; 15 and 20; 20 and 45; 20 and 40; 20 and 35; 20 and 30; 20 and 25; 25 and 45; 25 and 40; 25 and 35; or 25 and 30. The heating the dehydrated cannabis under oxygen-limited conditions may include heating for between about 20 minutes and about 40 minutes at a temperature of between about 135° C. and about 150° C.

In various embodiments, the heating the dehydrated cannabis under oxygen-limited conditions may include one or more of: heating the dehydrated cannabis in a container sealed against oxygen; heating the dehydrated cannabis under an atmosphere reduced in oxygen compared to air; heating the dehydrated cannabis under an inert atmosphere; heating the dehydrated cannabis in the presence of a volume of air in mL less than about 10 times a mass in grams of the dehydrated cannabis; heating the dehydrated cannabis in the presence of a volume of oxygen in mL less than about a mass in grams of the dehydrated cannabis; or heating the dehydrated cannabis in the presence of an oxygen getter.

In various embodiments, the heating the dehydrated cannabis under oxygen-limited conditions effective to form a roasted cannabis may be effective in decarboxylating at least a portion of tetrahydrocannabinolic acid included by the dehydrated cannabis to form tetrahydrocannabinol. The method may include decarboxylating a percentage of tetrahydrocannabinolic acid included by the dehydrated cannabis to form tetrahydrocannabinol included by the roasted cannabis. The percentage may be a percentage by weight of the tetrahydrocannabinolic acid included by the dehydrated cannabis, the percentage may be, or may be about one or more of: 70%; 75%; 80%; 85%; 90%; 91%; 92%; 93%; 94%; 95%; 96%; 97%; 98%; 99% or 100%; or a range between any two of the preceding values, for example, between about 70% and about 100%, between about 80% and about 99%, and the like.

In various embodiments, the heating the dehydrated cannabis under oxygen-limited conditions effective to form a roasted cannabis may be effective in isomerizing at least a portion of one or more delta-9 isomers to form one or more delta-11 isomers. The one or more delta-9 isomers may include one or more of delta-9 tetrahydrocannabinolic acid or delta-9 tetrahydrocannabinol. The one or more delta-11 isomers may include one or more of delta-11 tetrahydrocannabinolic acid or delta-11 tetrahydrocannabinol. The heating the dehydrated cannabis under oxygen-limited conditions effective to form a roasted cannabis may be effective in isomerizing a percentage of one or more delta-9 isomers to form one or more delta-11 isomers. The percentage may be a percentage by weight, the percentage may be, or may be about one or more of: 70%; 75%; 80%; 85%; 90%; 91%; 92%; 93%; 94%; 95%; 96%; 97%; 98%; 99% or 100%; or a range between any two of the preceding values, for example, between about 70% and about 100%, between about 80% and about 99%, and the like. The heating the dehydrated cannabis under oxygen-limited conditions effective to form a roasted cannabis may be effective in decarboxylating and isomerizing at least a portion of delta-9 tetrahydrocannabinolic acid included by the dehydrated cannabis to form delta-11 tetrahydrocannabinol. The method may include decarboxylating and isomerizing at least a percentage of delta-9 tetrahydrocannabinolic acid included by the dehydrated cannabis to form delta-11 tetrahydrocannabinol. The percentage may be a percentage by weight, the percentage may be, or may be about one or more of 70%; 75%; 80%; 85%; 90%; 91%; 92%; 93%; 94%; 95%; 96%; 97%; 98%; 99% or 100%; or a range between any two of the preceding values, for example, between about 70% and about 100%, between about 80% and about 99%, and the like.

In various embodiments, the combining the roasted cannabis with the ingestible hydrophobic excipient may include combining the roasted cannabis in a ratio to the ingestible excipient in a ratio of, or of about, one or more of: 1:10; 1:5; 3:10; 2:5; 1:2; 3:5; 7:10; 4:5; 9:10; 95:100; 1:1; 100:95; 10:9; 5:4; 10:7; 5:3; 2:1; 5:2; 10:3; 5:1; or 10:1; or a range between about any two of the preceding values, for example, between: 1:10 and 10:1; 1:5 and 5:1; 3:10 and 10:3; 2:5 and 5:2; 1:2 and 2:1; 3:5 and 5:3; 7:10 and 10:7; 4:5 and 5:4; 9:10 and 10:9; or 95:100 and 100:95.

In various embodiments, the combining the roasted cannabis with the ingestible hydrophobic excipient may include heating and mixing the roasted cannabis with the ingestible hydrophobic excipient to form a mixture; and cooling the mixture to form the ingestible cannabis composition. The method may include mixing the roasted cannabis with the ingestible hydrophobic excipient in hot water to form a mixture; and separating the ingestible cannabis composition from the water. The ingestible cannabis composition may include at least a portion of the ingestible hydrophobic excipient and at least a portion of the roasted cannabis. The hot water may be, or may be about, a temperature in ° C. of at least about one or more of about: 50; 55; 60; 65; 70; 75; 80; 85; 90; 91; 92; 93; 94; 95; 96; 97; 98; 99; or 100; or a range of any two of the preceding values, for example, about 80 to about 100, about 90 to about 100, and the like.

In various embodiments, the ingestible excipient may include one or more of: an animal fat; a vegetable oil; a vegetable wax; a polyethylene oxide; a polycarboxylate; a polyacrylamide; a gelatin; a polysaccharide; a polyvinylpyrrolidone; a crosscarmellose; a starch; hydroxypropyl cellulose; hydroxypropyl methylcellulose; or a polyethylene oxide. The ingestible excipient may be hydrophobic, e.g., may be partly or completely immiscible in water. The ingestible excipient may include coconut oil, for example, virgin coconut oil.

In various embodiments, the method may further include cooling the roasted cannabis. The method may include heating the dehydrated cannabis under oxygen-limited conditions effective to form the roasted cannabis and the cooling the roasted cannabis together including a heating-cooling cycle. The method may further include conducting at least one additional heating-cooling cycle. The cooling the roasted cannabis may include cooling the roasted cannabis to a temperature in ° C. of, of about, of less than, or of less than about: 40; 30; 25; 20; 15; 10; 5; 0; −5; −10; −15; −20; or −25; or a range of any of the preceding values, for example, about 10 to about 0, and the like. The cooling the roasted cannabis may be conducted before combining the roasted cannabis with the ingestible excipient to form the ingestible cannabis composition.

In various embodiments, the method may include may include processing one or more of: the cannabis, the dehydrated cannabis, the roasted cannabis, or the ingestible cannabis composition. The processing may include one or more of: grinding, chopping, cutting, comminuting, or cropping.

In various embodiments, an ingestible cannabis composition is provided. The ingestible cannabis composition may include a roasted cannabis. The ingestible cannabis composition may include an ingestible excipient to form the ingestible cannabis composition. The ingestible cannabis composition may be prepared by any method described herein.

In various embodiments, the roasted cannabis may be characterized by a ratio of tetrahydrocannabinol to tetrahydrocannabinolic acid of, or of about, at least one or more of: 1:10; 1:5; 3:10; 2:5; 1:2; 3:5; 7:10; 4:5; 9:10; 95:100; 1:1; 100:95; 10:9; 5:4; 10:7; 5:3; 2:1; 5:2; 10:3; 5:1; or 10:1; or a range between about any two of the preceding values, for example, between: 1:10 and 10:1; 1:5 and 5:1; 3:10 and 10:3; 2:5 and 5:2; 1:2 and 2:1; 3:5 and 5:3; 7:10 and 10:7; 4:5 and 5:4; 9:10 and 10:9; or 95:100 and 100:95.

In various embodiments, the roasted cannabis may be characterized by a ratio of one or more delta-11 isomers to one or more delta-9 isomers of at least one or more of, or of about: 3:1; 4:1; 5:1; 6:1; 7:1; 8:1; 9:1; 10:1; 15:1; 20:1; 25:1; 50:1; or 100:1; or a range between about any two of the preceding values, for example, between 3:1 and 100:1, and the like. The one or more delta-9 isomers may include one or more of delta-9 tetrahydrocannabinolic acid or delta-9 tetrahydrocannabinol. The one or more delta-11 isomers may include one or more of delta-11 tetrahydrocannabinolic acid or delta-11 tetrahydrocannabinol. The roasted cannabis may be characterized by a ratio of delta-11 tetrahydrocannabinol to delta-9 tetrahydrocannabinolic acid of at least one or more of about: 3:1; 4:1; 5:1; 6:1; 7:1; 8:1; 9:1; 10:1; 15:1; 20:1; 25:1; 50:1; or 100:1; or a range between about any two of the preceding values, for example, between 3:1 and 100:1, and the like.

In various embodiments, the ingestible excipient may include one or more of: an animal fat; a vegetable oil; a vegetable wax; a polyethylene oxide; a polycarboxylate; a polyacrylamide; a gelatin; a polysaccharide; a polyvinylpyrrolidone; a crosscarmellose; a starch; hydroxypropyl cellulose; hydroxypropyl methylcellulose; or a polyethylene oxide. The ingestible excipient may be hydrophobic, e.g., may be partly or completely immiscible in water. The ingestible excipient may include coconut oil, for example, virgin coconut oil. The roasted cannabis may be in a ratio to the ingestible excipient in a ratio of, or of about, one or more of: 1:10; 1:5; 3:10; 2:5; 1:2; 3:5; 7:10; 4:5; 9:10; 95:100; 1:1; 100:95; 10:9; 5:4; 10:7; 5:3; 2:1; 5:2; 10:3; 5:1; or 10:1; or a range between about any two of the preceding values, for example, between: 1:10 and 10:1; 1:5 and 5:1; 3:10 and 10:3; 2:5 and 5:2; 1:2 and 2:1; 3:5 and 5:3; 7:10 and 10:7; 4:5 and 5:4; 9:10 and 10:9; or 95:100 and 100:95.

In various embodiments, the roasted cannabis may include a dehydrated cannabis heated under oxygen-limited conditions effective to form the roasted cannabis. The dehydrated cannabis may be characterized by dehydration including one or more of: oven drying; sun drying; forced-air drying; drum drying; freeze-drying; vacuum desiccation; chemical desiccation; or supercritical desiccation. The dehydrated cannabis may be characterized by a moisture content in weight percent of less than, or less than about one or more of: 50; 45; 40; 35; 30; 25; 20; 19; 18; 17; 16; 15; 14; 13; 12; 11; 10; 9; 8; 7; 6; 5; 4; 3; 2; 1; or 0.5; or a range between any two of the preceding values, for example, between about 50% and about 0.5%, between about 30% and about 0.5%, between about 20% and about 0.5%, and the like. The roasted cannabis may include a dehydrated cannabis heated under oxygen-limited conditions effective to form the roasted cannabis at a temperature in ° C. of, or of about, one or more of: 115; 120; 125; 130; 130; 131; 132; 133; 134; 135; 136; 137; 138; 138; 140; 141; 142; 143; 144; 145; 146; 147; 148; 149; 150; 155; or 160; or a range of, or a range about, any two of the preceding values in ° C. For example, the temperature range in ° C. may be between about one or more of: 115 and 155; 120 and 155; 120 and 150; 125 and 155; 125 and 150; 125 and 145; 130 and 155; 130 and 150; 130 and 145; 130 and 140; 135 and 155; 135 and 150; 135 and 145; or 135 and 140. In some embodiments, the temperature in ° C. may be, or may be about, one or more of: 130; 131; 132; 133; 134; 135; 136; 137; 138; 138; 140; 141; 142; 143; 144; 145; 146; 147; 148; 149; or 150. In some embodiments, the temperature in ° C. may be, or may be about, one or more of: 135; 136; 137; 138; 138; 140; 141; 142; 143; 144; or 145.

The roasted cannabis may include a dehydrated cannabis heated under oxygen-limited conditions effective to form the roasted cannabis for a time range in minutes of, or of about, one or more of: 15; 20; 25; 30; 35; 40; 45; 50; 55; 60; 90; or 120; or a range between any two of the preceding values, for example, about or between about one or more of: 15 and 55; 15 and 50; 15 and 45; 15 and 40; 15 and 35; 15 and 30; 15 and 25; 15 and 20; 20 and 45; 20 and 40; 20 and 35; 20 and 30; 20 and 25; 25 and 45; 25 and 40; 25 and 35; or 25 and 30. The roasted cannabis may include a dehydrated cannabis heated under oxygen-limited conditions for between about 20 minutes and about 40 minutes at a temperature of between about 135° C. and about 150° C. The roasted cannabis may include a dehydrated cannabis heated under oxygen-limited conditions effective to form the roasted cannabis characterized by one or more of: the dehydrated cannabis heated in a container sealed against oxygen; the dehydrated cannabis heated under an atmosphere reduced in oxygen compared to air; the dehydrated cannabis heated under an inert atmosphere; the dehydrated cannabis heated in the presence of a volume of air in mL less than about 10 times a mass in grams of the dehydrated cannabis; the dehydrated cannabis heated in the presence of a volume of oxygen in mL less than about a mass in grams of the dehydrated cannabis; or the dehydrated cannabis heated in the presence of an oxygen getter.

In various embodiments, the ingestible cannabis composition may be characterized by the roasted cannabis having been mixed with the ingestible hydrophobic excipient in hot water to form a mixture; and the ingestible cannabis composition having been separated from the water.

In various embodiments, one or more of: the cannabis, the dehydrated cannabis, the roasted cannabis, or the ingestible cannabis composition may be processed. "Processed" may include one or more of: ground, chopped, cut, comminuted, or cropped.

Figure 2:
FIG. 2 is a block diagram describing an example kit.

In various embodiments, a kit is provided. FIG. 2 is a block diagram describing an example kit 200. Kit 200 may include 202 an ingestible cannabis composition including a roasted cannabis and an ingestible excipient. Kit 200 may include 204 instructions. The instructions may include directing a user to ingest a portion of the ingestible cannabis composition effective to provide the user with a desired dosage. The ingestible cannabis composition may be prepared by any method described herein. The ingestible cannabis composition may include any ingestible cannabis composition described herein.

Example

Cropped cannabis was obtained for drying. A portion of the cropped cannabis was dried in an oven at about 38° C. to form dehydrated cannabis. Another portion was shelf-dried for a period of time to form dehydrated cannabis. Each portion was judged dehydrated when it easily crumbled into smaller bits. It was observed in several related experiments that moisture removal surprisingly aided the subsequent conversion of delta-9 tetrahydrocannabinolic acid to delta-11 tetrahydrocannabinol. In some experiments, the amount of moisture removed approximately correlated with the extent of conversion of delta-9 tetrahydrocannabinolic acid to delta-11 tetrahydrocannabinol.

The dehydrated cannabis was placed in a plastic oven basting bag. The bag was sealed with a twist tie. The sealed bag included a portion of air along with the dehydrated cannabis. It was observed in other experiments that unsealed bags surprisingly did not perform as well as sealed bags in the subsequent conversion of delta-9 tetrahydrocannabinolic acid to delta-11 tetrahydrocannabinol. The sealed bag including the dehydrated cannabis was placed in an oven at about 143° C. It was observed in several related experiments that the conversion of delta-9 tetrahydrocannabinolic acid to delta-11 tetrahydrocannabinol was surprisingly improved starting at a temperature of about 132° C., with the best conversion occurring between about 135° C.-145° C., and preferably between about 140° C.-145° C. It was observed in several related experiments that placing the bag on parchment paper or an insulated cooking pan surprisingly improved the subsequent conversion of delta-9 tetrahydrocannabinolic acid to delta-11 tetrahydrocannabinol.

The sealed bag including the dehydrated cannabis was heated for 20 to 30 minutes. The cannabis plant material was observed to expand or "pop open" during the heating process.

The sealed bag including now-roasted cannabis was removed after heating. In some experiments, the roasted cannabis was used without further oven heating. In some experiments, the roasted cannabis was removed from the oven in the oven bag, cut open to vent any accumulated moisture on the inside of the oven bag, and placed in a freezer at about ° C. for about 2 hours. Once cold, the roasted cannabis was placed a new oven bag and subjected to a second heating cycle.

The roasted cannabis was boiled together with virgin coconut oil, then let simmer and cool until the roasted cannabis and virgin coconut oil hardened together to form an ingestible cannabis composition.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A method for preparing an ingestible cannabis composition, comprising:
   a) dehydrating cannabis to provide a dehydrated cannabis;
   b) heating the dehydrated cannabis under oxygen limited conditions for between about 20 minutes and about 40 minutes at a temperature of between about 130° C. and about 150° C. to form a roasted cannabis, wherein the heating of the dehydrated cannabis is performed under oxygen-limited conditions comprising one or more of: heating the dehydrated cannabis in a container sealed against oxygen; and heating the dehydrated cannabis under an inert atmosphere containing little or no oxygen;
   c) mixing the roasted cannabis with an ingestible excipient in hot water to form a mixture of cannabis and ingestible excipient and separating the ingestible excipient and the roasted cannabis from the water to form the ingestible cannabis composition, wherein the ingestible excipient is selected from the group consisting of animal fat, vegetable oil, vegetable wax, polyethylene oxide, polycarboxylate, polyacrylamide, gelatin, polysaccharide, polyvinylpyrrolidone, crosscarmellose, starch, hydroxypropyl cellulose, hydroxypropyl methylcellulose, and virgin coconut oil.

2. The method of claim 1, wherein the dehydrated cannabis is heated to a temperature of between about 132° C. and about 150° C.

3. The method of claim 1, wherein the dehydrated cannabis is heated to a temperature of between about 135° C. and about 145° C.

4. The method of claim 1, wherein the dehydrated cannabis is heated to a temperature of between about 140° C. and about 145° C.

5. The method of claim 1, wherein the cannabis is dehydrated by one or more of: oven drying; sun drying; forced-air drying; drum drying; freeze-drying; vacuum desiccation; chemical desiccation; and supercritical desiccation.

6. The method of claim 1, wherein the dehydrated cannabis has a moisture content in weight percent of less than about 50%.

7. The method of claim 1, wherein the dehydrated cannabis has a moisture content in weight percent of less than about 15%.

8. The method of claim 1, wherein the dehydrated cannabis has a moisture content in weight percent of less than about 12%.

9. The method of claim 1, wherein the dehydrated cannabis has a moisture content in weight percent of less than about 10%.

10. The method of claim 1, wherein the heating of the dehydrated cannabis to form the roasted cannabis decarboxylates and isomerizes at least a portion of the delta-9 tetrahydrocannabinolic acid in the cannabis to form delta-11 tetrahydrocannabinol.

11. The method of claim 1, wherein the roasted cannabis has a ratio of tetrahydrocannabinol to tetrahydrocannabinolic acid of at least about 3:1.

12. The method of claim 1, wherein the roasted cannabis has a ratio of delta-11 tetrahydrocannabinol to delta-9 tetrahydrocannabinolic acid of at least about 3:1.

13. The method of claim 1, wherein the roasted cannabis and the ingestible excipient in the hot water are mixed at a temperature of at least about 50° C.

14. The method of claim 1, wherein the roasted cannabis and the ingestible excipient are mixed in the boiling water.

15. The method of claim 1, further comprising:
    cooling the hot water to form cooled water; and
    separating the cooled water from the ingestible cannabis composition.

16. The method of claim 1, wherein the roasted cannabis is mixed in a ratio to the ingestible excipient in a range of between about 1:10 and 10:1.

17. The method of claim 1, further comprising at least two heating-cooling cycles, each heating-cooling cycle comprising:
    heating the dehydrated cannabis to form the roasted cannabis; and
    cooling the roasted cannabis.

18. The method of claim 17, wherein the roasted cannabis is cooled in at least one said heating-cooling cycle to a temperature of less than about 40° C.

19. The method of claim 17, wherein the roasted cannabis is cooled in at least one said heating-cooling cycle to a temperature of less than about 0° C.

20. The method of claim 17, wherein accumulated moisture is removed from the roasted cannabis in at least one said heating-cooling cycle.

* * * * *